US00PP25297P3

(12) United States Plant Patent
Lavi et al.

(10) Patent No.: US PP25,297 P3
(45) Date of Patent: Feb. 24, 2015

(54) MANGO TREE NAMED 'NOA'

(50) Latin Name: ***Mangifera indica* L.**
Varietal Denomination: NOA

(71) Applicant: State of Israel, Ministry of Agriculture & Rural Development, Agricultural Research Organization, Bet Dagan (IL)

(72) Inventors: Uri Lavi, Rehovot (IL); Eli Tomer, Mazkeret Batia (IL); David Saada, Rishon Lezion (IL); Yuval Cohen, Mesilat Zion (IL)

(73) Assignee: State of Israel, Ministry of Agriculture & Rural Development, Agricultural Research Organization, Bet Dagan (IL)

( * ) Notice: Subject to any disclaimer, the term of this patent is extended or adjusted under 35 U.S.C. 154(b) by 39 days.

(21) Appl. No.: 13/815,241

(22) Filed: Feb. 13, 2013

(65) Prior Publication Data

US 2014/0230106 P1 Aug. 14, 2014

(51) Int. Cl.
*A01H 5/00* (2006.01)

(52) U.S. Cl.
USPC ..... Plt./159

(58) Field of Classification Search
USPC ..... Plt./159
See application file for complete search history.

(56) References Cited

PUBLICATIONS

PLUTO Plant Variety Database 2014-04 search for cultivar NOA. p. 1.*

* cited by examiner

*Primary Examiner* — Annette Para
(74) *Attorney, Agent, or Firm* — Foley & Lardner LLP

(57) ABSTRACT

A new and distinct late ripening variety of mango tree (*Mangifera indica* L.) named 'NOA', particularly characterized by attractive fruit shape and color, excellent internal quality and low amount of fiber.

4 Drawing Sheets

Figure 1:
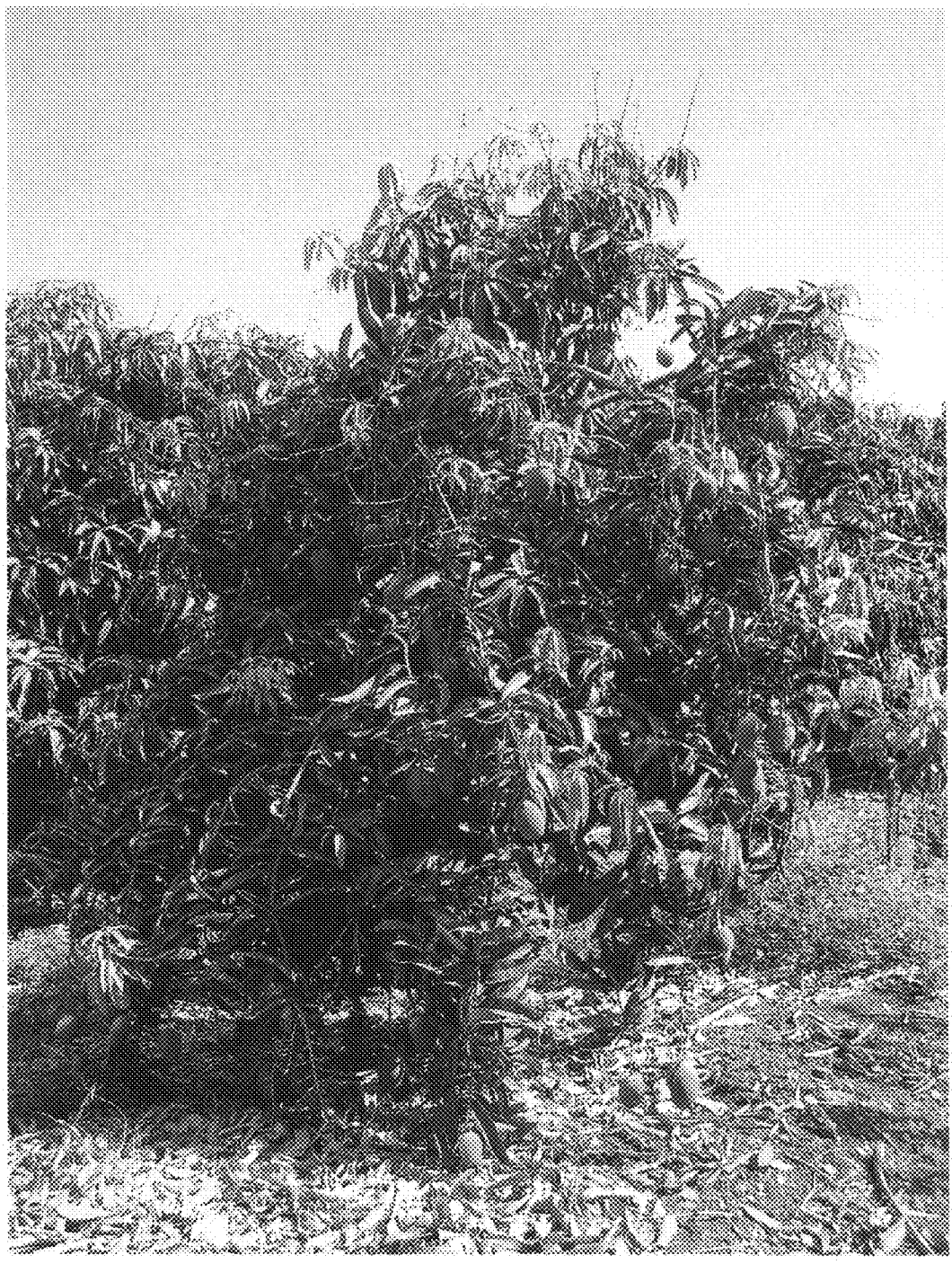

Botanical name of the genus and species of the plant claimed: *Mangifera indica* L.

Variety denomination: 'NOA'.

BACKGROUND OF THE INVENTION

The present invention relates to a new and distinct variety of a mango plant, botanically known as *Mangifera indica* L. of the Anacardiaceae family, and hereinafter referred to by the variety denomination 'NOA'.

The new *Mangifera indica* L. variety 'NOA' is a product of a planned breeding program conducted by the inventors, Uri Lavi, Eli Tomer, David Saada, and Yuval Cohen at the Volcani Center, Bet Dagan, Israel. The objective of the breeding program was to develop a new, late ripening, *Mangifera indica* L. variety with attractive fruit shape and color, excellent internal quality and low amount of fiber.

The new *Mangifera indica* L. variety 'NOA' originated from open pollination of the *Mangifera indica* L. variety 'SHELLY' (registered, Israel Plant Breeders' Rights registration No. 2549; European CPVO Grant No. 21160) in the inventors' collection in 1995 in the Volcani Center, Bet Dagan, Israel. The new *Mangifera indica* L. 'NOA' was observed and selected by the inventors within the progeny of this open pollination in a controlled environment in 2001 in the Volcani Center, Bet Dagan, Israel.

Asexual propagation of the new *Mangifera indica* L. variety by grafting onto *Mangifera indica* L. rootstock '13/1' (unpatented) was first performed in May 2002 in the Volcani Center, Bet Dagan, Israel, and has demonstrated that the combination of characteristics as herein disclosed for the new variety is firmly fixed and retained through successive generations of asexual propagation. The new variety propagates true-to-type.

BRIEF DESCRIPTION OF THE INVENTION

The following characteristics have been repeatedly observed and are determined to be characteristics of 'NOA', which in combination, distinguish this mango tree as a new, unique and distinct variety:

1. Relatively late ripening;
2. Attractive fruit shape and color;
3. Excellent internal quality; and
4. Low amount of fiber.

In comparison to the maternal parent variety, 'SHELLY' (registered, Israel Plant Breeders' Rights registration No. 2549; European CPVO Grant No. 21160), 'NOA' differs primarily in the traits listed in Table 1.

TABLE 1

Comparison with female parent.

| Trait | New Variety 'NOA' | Female Parent 'SHELLY' (registered) |
|---|---|---|
| Young leaf anthocyanin coloration | medium | very weak to weak |
| Inflorescence length | long | very short |

TABLE 1-continued

| Comparison with female parent. | | |
|---|---|---|
| Trait | New Variety 'NOA' | Female Parent 'SHELLY' (registered) |
| Mature fruit ratio length/width | small to medium | very small |
| Mature fruit color of skin | green and red | green and purple |
| Ripe fruit color of skin | orange and red | orange and purple |

Of the many commercial varieties known to the present inventors, the most similar in comparison to the new *Mangifera indica* L. 'NOA' is *Mangifera indica* L. 'KEITT' (unpatented) which differ from the new mango 'NOA' in the characteristics described in Table 2:

TABLE 2

| Comparison with a well known commercial variety. | | |
|---|---|---|
| Characteristic | New Variety 'NOA' | Comparison Variety 'KEITT' (unpatented) |
| Mature fruit shape of ventral shoulder | rounded upwards | rounded downwards |
| Stone relief of surface | ridged | grooved |
| Mature fruit color of skin | red, yellow and green | green |

BRIEF DESCRIPTION OF THE PHOTOGRAPHS

The accompanying photographs illustrate the overall appearance of the new *Mangifera indica* L. variety 'NOA' showing the colors as true as is reasonably possible with colored reproductions of this type. Colors in the photographs may differ slightly from the color values cited in the detailed morphological description, which accurately describe the color of 'NOA'.

FIG. 1—Shows a fruit-bearing tree of 'NOA'.

Figure 2:
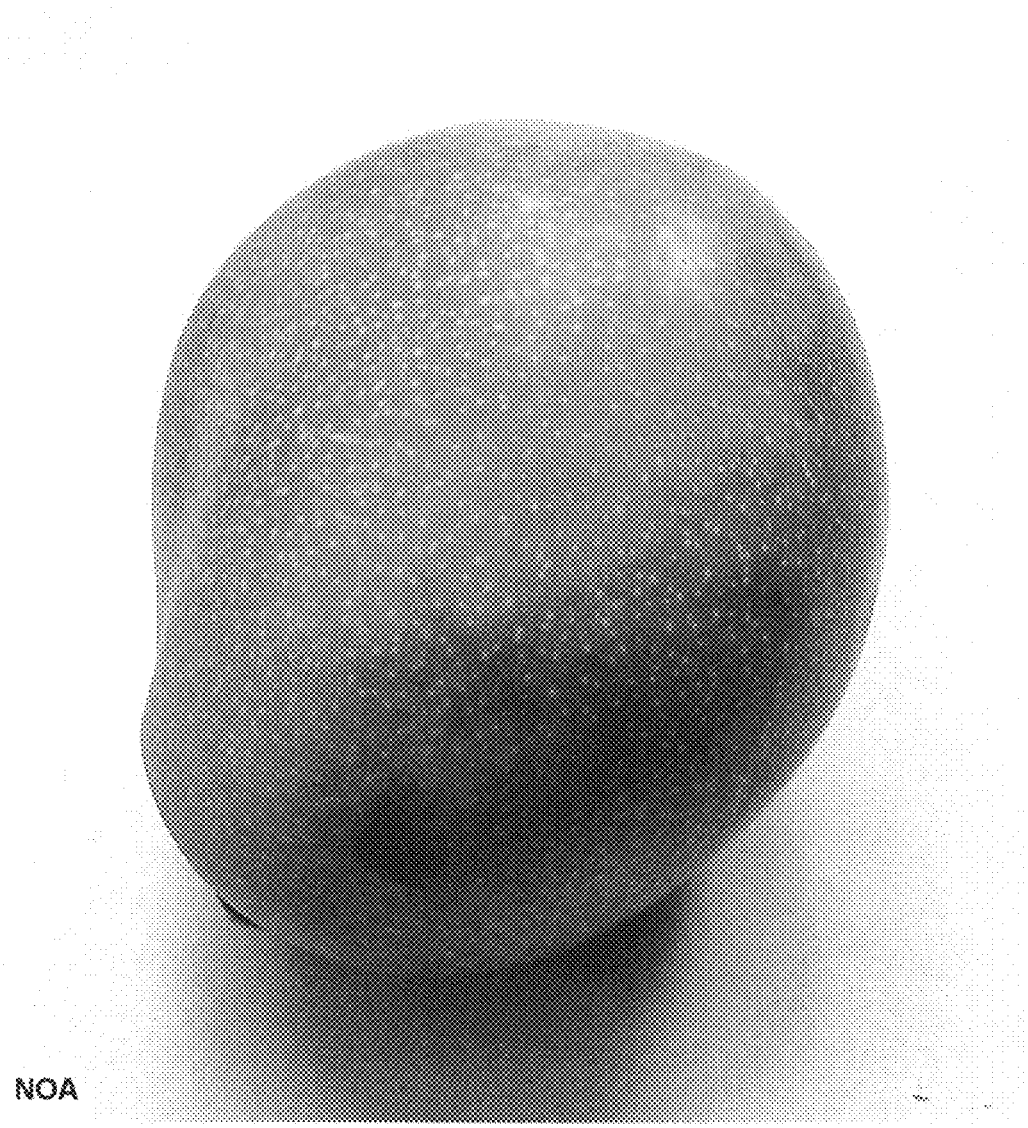

FIG. 2—Shows typical mature fruit of 'NOA'.

Figure 3:
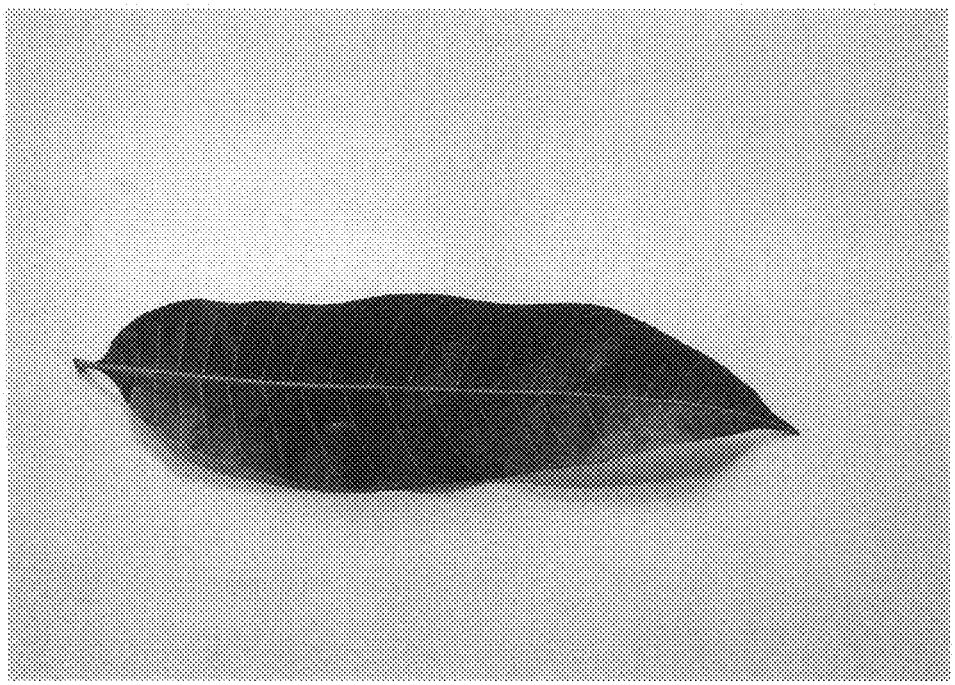

FIG. 3—Shows typical leaf of 'NOA'.

Figure 4:
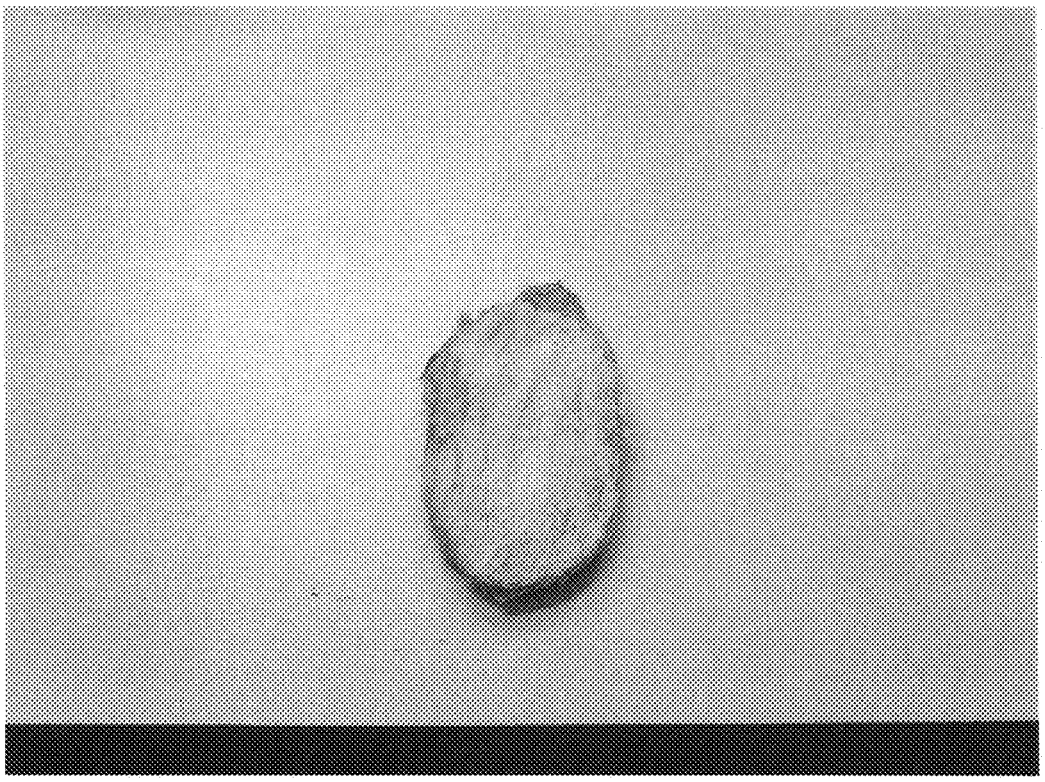

FIG. 4—Shows typical stone of 'NOA'.

DETAILED MORPHOLOGICAL DESCRIPTION

The new *Mangifera indica* L. variety 'NOA' has not been observed under all possible environmental conditions. The phenotype of the new variety may vary with variations in environment such as temperature, light intensity, day length, soil or pruning without any change in the genotype of the mango plant.

The aforementioned photographs, together with the following observations, measurements and values describe trees of 'NOA' as grown in the orchard at the Volcani Center, Bet Dagan, Israel, under conditions which closely approximate those generally used in commercial practice. The described trees were grafted on *Mangifera indica* L. rootstock '13/1' (unpatented) and planted at a distance of 4×5 m in sandy red loam soil at an elevation of about 30 meters above sea level, irrigated with 6000 $m^3$/hectare and fertilized with 1 liter/5 $m^3$ of "sheffer" N:P:K 7:3:7". Average annual rainfall is about 550 mm, with an average 350 mm of rainfall in winter (December to February). Mean diurnal minimum temperature in January is 7.2° C., and mean diurnal maximum temperature in July is 30.8° C.

Unless otherwise stated, the detailed morphological description includes observations, measurements and values taken from 2010 to 2012 and based on four-year-old 'NOA' trees grown in the orchard at the Volcani Center, Bet Dagan, Israel. Quantified measurements are expressed as an average or a range of measurements taken from a number of plants of 'NOA'. The measurements of any individual plant, or any group of plants, of the new variety may vary from the stated average or range.

Color references are made to The Royal Horticultural Society Colour Chart (R.H.S.), (1986 edition), except where general colors of ordinary significance are used. Color values were taken under daylight conditions in full sunlight in the Volcani Center, Bet Dagan, Israel.

All of the trees of 'NOA', insofar as they have been observed, have been consistent in all the characteristics described below.

Classification:

*Botanical.*—*Mangifera indica* L.

Parentage:

*Female or seed parent.*—*Mangifera indica* L. 'SHELLY' (registered).

*Male or pollen parent.*—Unknown.

Propagation: Grafting onto *Mangifera indica* L. rootstock '13/1' (unpatented).

*Pollination requirements.*—None.

Growing conditions:

*Light intensities.*—Full sunlight. Irrigated with 6000 $m^3$/hectare.

| | January | February | March | April | May | June |
|---|---|---|---|---|---|---|
| Mean maximum air temperature (° C.) | 17.8 | 18.1 | 20.1 | 24.5 | 27 | 29.2 |
| Mean minimum air temperature (° C.) | 7.2 | 7.1 | 8.8 | 11.5 | 14.6 | 17.9 |
| Mean rainfall (mm) | 140.5 | 96.9 | 66.1 | 17.5 | 2.2 | — |

| | July | August | September | October | November | December |
|---|---|---|---|---|---|---|
| Mean maximum air temperature (° C.) | 30.8 | 31.2 | 30.4 | 28.3 | 24.1 | 19.7 |
| Mean minimum air temperature (° C.) | 20.6 | 21.2 | 19.4 | 16 | 11.8 | 8.6 |
| Mean rainfall (mm) | — | — | 0.4 | 20.4 | 76.2 | 130.3 |

*Fertilization.*—A balanced fertilizer with level of N:P:K 7:3:7.

*Growth regulators.*—Not applied.

*Pruning or trimming.*—As in commercial practice.

TABLE OF CHARACTERISTICS

Tree:
- *Age*.—Observed trees were four years old.
- *Vigor*.—Very strong.
- *Height*.—About 3 m.
- *Diameter of crown*.—About 3 m.
- *General shape of canopy*.—Cylindrical.
- *Number of main brunches*.—2.
- *Attitude of main brunches*.—Semi upright.
- *Diameter of trunk*.—About 30 cm at 1 m height.
- *Surface of trunk*.—Cracked.
- *Trunk lenticels*.—Not visible.
- *Trunk color of bark*.—Light brownish gray RHS 199 D.

Main branch:
- *Length*.—About 2.5 m.
- *Diameter*.—About 15 cm.
- *Surface*.—Smooth.
- *Lenticels*.—Not visible.
- *Color*.—Light brownish gray RHS 199 C.

Young leaf:
- *Length*.—15-23 cm.
- *Width*.—34-43 mm.
- *Shape*.—Elliptic.
- *Color of upper side*.—Brown-bronze between RHS 199 A and RHS 199 B.
- *Color of lower side*.—Brown-bronze RHS 199 A.
- *Color of main vein of upper side*.—Light brown RHS 199 B.
- *Color of main vein of lower side*.—Light green RHS 144 C.
- *Color of secondary veins at both sides*.—Light green RHS 144 C.

Petiole of young leaf:
- *Length*.—30-40 mm.
- *Cross section*.—Flat.
- *Pubescence*.—Weak.
- *Color of upper side*.—Light brown RHS 199 B.
- *Color of lower side*.—Light green RHS 144 C.

Mature leaf blade:
- *Length*.—21-24 cm.
- *Width*.—6-8 cm.
- *Length/width ratio*.—Small.
- *Shape*.—Ovate.
- *Color of upper side*.—Dark green RHS 146 A.
- *Color of lower side*.—Light to medium green RHS 146 D.
- *Twisting of blade*.—Absent.
- *Spacing of secondary veins*.—Ca. 10 mm.
- *Undulation of margin*.—Medium.
- *Shape of base*.—Acute.
- *Shape of apex*.—Acute.

Petiole of mature leaf:
- *Attitude in relation to shoot*.—Perpendicular.
- *Length*.—15-20 mm.

Inflorescence:
- *Length*.—Ca. 30 cm.
- *Diameter*.—Ca. 22 cm.
- *Ratio length/diameter*.—Large.
- *Thickness of main axis*.—8-9 mm.
- *Pubescence*.—Medium dense.
- *Shape*.—Elongated.
- *Color of main axis and brunches*.—Dark reddish brown RHS 181 A.
- *Number of primary branches*.—Few.
- *Anthocyanin coloration of axis and branches of first order*.—Strong, dark reddish brown RHS 182 A.
- *Anthocyanin coloration of side branches of tertiary order*.—Reddish brown between RHS 181 B and RHS 181 C.
- *Length of lowest side branch*.—15-18 cm.
- *Thickness of lowest side branch*.—3-4 mm.

Flower:
- *Number of petals*.—Five.
- *Length*.—5 mm.
- *Diameter*.—5-6 mm.
- *Shape viewed from above*.—Stellate.

Petal:
- *Length*.—2 mm.
- *Width*.—1 mm.
- *Shape*.—Ovate.
- *Color on both sides*.—Yellowish green RHS 2 C.

Calyx:
- *Shape*.—Bowl shaped.
- *Number of sepals*.—Five.
- *Color of sepal*.—Yellowish green RHS 145 B.
- *Shape of sepal*.—Triangular.

Style:
- *Number*.—One.
- *Length*.—Ca. 2 mm.
- *Thickness*.—Very thin.
- *Color*.—Yellowish RHS 2 CD.

Stigma:
- *Size*.—Minuscule.

Stamen:
- *Size*.—Very small.

Anther:
- *Color*.—Brownish.

Mature fruit:
- *Length*.—13-14 cm.
- *Width*.—9-10 cm.
- *Ratio length/width*.—Small to medium.
- *Thickness*.—8-9 cm.
- *Weight*.—500-600 g.
- *Shape in cross section*.—Broad elliptic.
- *Color of skin*.—Green RHS 137 C and red between RHS 184 B and RHS 184 C.
- *Waxiness*.—Medium.
- *Density of lenticels*.—Medium.
- *Shape of lenticel*.—Rounded.
- *Color of lenticel*.—Very light green between RHS 138 C and RHS 138 D.
- *Color contrast between lenticel and skin*.—Strong.
- *Size of lenticel*.—Pin-head.
- *Surface*.—Smooth.
- *Stalk cavity*.—Absent or shallow.
- *Presence of neck*.—Absent.
- *Shape of ventral shoulder*.—Rounded upwards.
- *Shape of dorsal shoulder*.—Sloping downwards.
- *Length of groove in ventral shoulder*.—Absent.
- *Bulging on ventral shoulder*.—Absent.
- *Depth of sinus*.—Medium.
- *Bulge proximal of stylar scar*.—Medium.
- *Point at stylar scar*.—Absent or small.
- *Diameter of stalk attachment*.—Medium to large.

Ripe fruit:
- *Predominant color of skin*.—Orange RHS 180 B.
- *Speckling of skin*.—Absent or very weak.
- *Thickness of skin*.—Ca. 3 mm.
- *Adherence of skin to flesh*.—Strong.

*Main color of flesh*.—Medium orange RHS 21 B.
*Firmness of flesh*.—Firm.
*Juiciness*.—Medium.
*Amount of fiber attached to stone*.—Low.
*Amount of fiber attached to skin*.—Low.
*Turpentine flavor*.—Absent.

Stone:
*Length*.—Ca. 10 cm.
*Width*.—Ca. 5 cm.
*Thickness*.—Ca. 2 cm.
*Density of fiber*.—Lax.
*Length of fiber*.—5-10 mm.
*Color*.—Beige RHS 158 A.
*Relief of surface*.—Weakly ridged.

Seed:
*Shape in lateral view*.—Reniform.
*Embryony*.—Monomembryonic.
*Time of beginning of flowering*.—Spring.
*Time of fruit maturity*.—About August $20^{th}$ to September $20^{th}$.

Tree:
Disease resistance: No atypical resistance has been noted.
Pest resistance: No atypical resistance has been noted.
Disease susceptibility: None observed.
Pest susceptibility: None observed.

We claim:

1. A new and distinct *Mangifera indica* L. plant variety named 'NOA', as illustrated and described herein.

* * * * *